United States Patent [19]

Reiners et al.

[11] Patent Number: 4,952,614

[45] Date of Patent: Aug. 28, 1990

[54] (METH)ACRYLIC ACID DERIVATIVES, CONTAINING URETHANE GROUPS, OF TRICYCLO[5.2.1.0$^{2.6}$]DECANES

[75] Inventors: Jürgen Reiners, Leverkusen; Wolfgang Podszun; Jens Winkel, both of Cologne, all of Fed. Rep. of Germany

[73] Assignee: Bayer Aktiengesellschaft, Leverkusen, Fed. Rep. of Germany

[21] Appl. No.: 313,925

[22] Filed: Feb. 22, 1989

Related U.S. Application Data

[63] Continuation of Ser. No. 72,185, Jul. 10, 1987, abandoned.

[30] Foreign Application Priority Data

Jul. 25, 1986 [DE] Fed. Rep. of Germany ....... 3625204
Feb. 3, 1987 [DE] Fed. Rep. of Germany ....... 3703120

[51] Int. Cl.$^5$ .......................... A61K 6/08; A61C 5/00
[52] U.S. Cl. .................................. 523/115; 433/228.1; 526/301
[58] Field of Search ........................... 106/35; 523/115

[56] References Cited

U.S. PATENT DOCUMENTS

| | | | |
|---|---|---|---|
| 4,379,695 | 4/1983 | Orlowski | 433/217.1 |
| 4,406,625 | 9/1983 | Orlowski | 433/228.1 |
| 4,554,336 | 11/1985 | Kidd | 526/301 |

*Primary Examiner*—Christopher Henderson
*Attorney, Agent, or Firm*—Sprung Horn Kramer & Woods

[57] ABSTRACT

The new (meth)acrylic acid derivatives, containing urethane groups, of tricyclo[5.2.1.0$^{2.6}$]decanes can be prepared by reaction of hydroxyalkyl (meth)acrylic acid esters with diisocyanates and subsequent reaction with polyols. The compounds can be used for dental materials.

7 Claims, No Drawings

(METH)ACRYLIC ACID DERIVATIVES, CONTAINING URETHANE GROUPS, OF TRICYCLO[5.2.1.0$^{2.6}$]DECANES

This is a continuation of application Ser. No. 072,185, filed July 10, 1987, now abandoned.

The invention relates to new (meth)acrylic acid derivatives, containing urethane groups, of tricyclo[5.2.1.0$^{2.6}$]decanes, to their preparation and to their use as monomeric components for dental materials.

BACKGROUND OF THE INVENTION

The use of polyfunctional (meth)acrylic acid derivatives as components for tooth-filling materials is known. Thus, in EP-A No. 0,017,936, acrylic acid esters and methacrylic acid esters of pentaerythritol are described. In combination with inorganic fillers, the monomers described therein provide dental materials which show undesired shrinkage on polymerization, causing the formation of a gap between the tooth material and the filling material.

In U.S. Pat. No. 4,554,336, (meth)acrylic acid derivatives containing urethane groups are described for adhesives in the dental field, wherein the urethane groups are substituted by a radical containing a (meth)acrylate group. These compounds as components in dental compositions show inadequate properties, in particular a strength which is too low for use in practice.

THE INVENTION

New (meth)acrylic acid derivatives, containing urethane groups, of the formula (I)

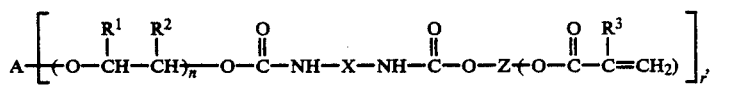

wherein

A is a straight-chain or branched aliphatic radical having 2 to 20 carbon atoms and optionally containing 1 to 3 oxygen bridges, an aromatic radical having 6 to 24 carbon atoms, an araliphatic radical having 7 to 26 carbon atoms or a cycloaliphatic radical having 6 to 26 carbon atoms, r represents the number of chains starting from A and denotes a number from 2 to 6, $R^1$ and $R^2$ are identical and denote hydrogen or are different and denote hydrogen and methyl, n denotes a number from 0 to 5, independently for each chain starting from A, X represents the group

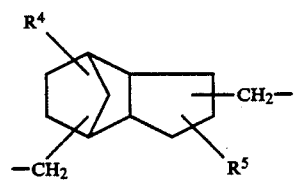

wherein $R^4$ and $R^5$ are identical or different and denote hydrogen, halogen, lower alkoxy, lower alkyl or trifluoromethyl, Z denotes a divalent straight-chain or branched aliphatic hydrocarbon radical which has 3 to 15 carbon atoms, can optionally contain 1 to 3 oxygen bridges and can optionally be substituted by 1 to 4 additional (meth)acrylate radicals, and $R^3$ denotes hydrogen or methyl, independently for each chain starting from A, have been found.

Dental materials for which the starting materials are the (meth)acrylic acid derivatives, containing urethane groups, of tricyclo[5.2.1.0$^{2.6}$]decanes, according to the invention, surprisingly show a substantially smaller shrinkage on polymerization and a higher strength and are therefore particularly suitable for use in practice.

Within the scope of the present invention, the substituents can have the following meanings:

An aliphatic radical (A) can be a straight-chain or branched hydrocarbon radical having 2 to 20, preferably 3 to 12, carbon atoms. The following aliphatic radicals may be mentioned as examples:

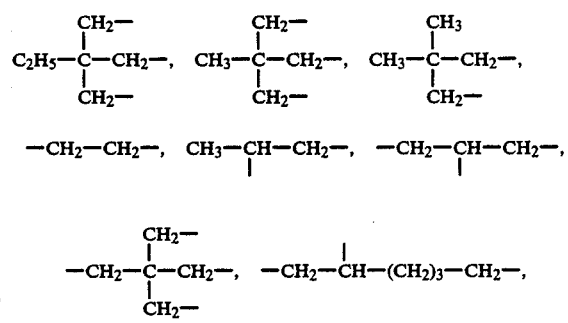

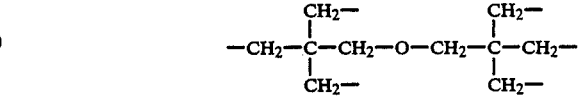

An aromatic radical (A) can be an aromatic hydrocarbon radical having 6 to 24, preferably 6 to 14, carbon atoms. The following aromatic radicals may be mentioned as examples:

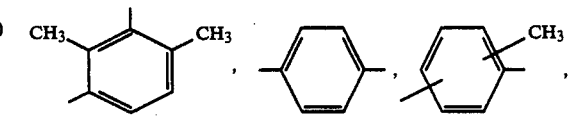

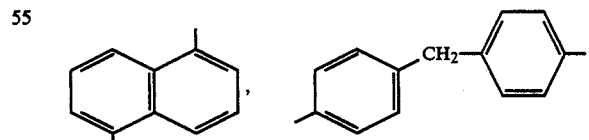

An araliphatic radical (A) can denote a hydrocarbon radical having 7 to 26 carbon atoms with a straight-chain or branched aliphatic part and an aromatic part, the aromatic part preferably having 6 to 12 carbon atoms and the aliphatic part preferably having 1 to 14 carbon atoms. The following araliphatic radicals may be mentioned as examples:

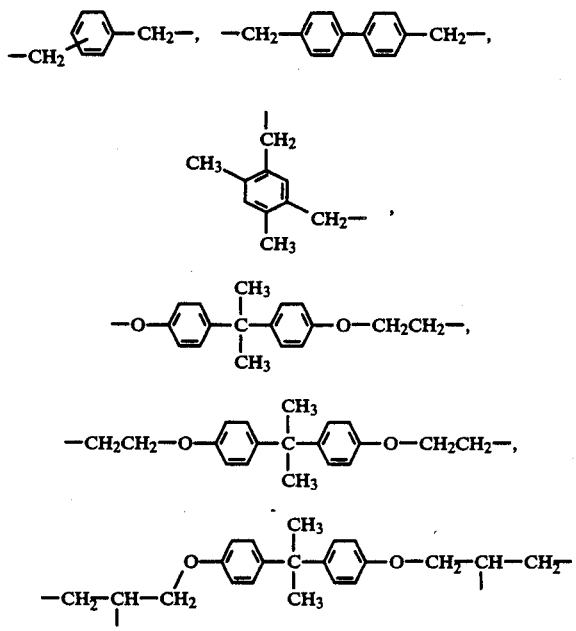

A cycloaliphatic radical (A) can be a cyclic hydrocarbon radical having 6 to 26 carbon atoms, preferably 6 to 14 carbon atoms. The following cycloaliphatic radicals mentioned as examples:

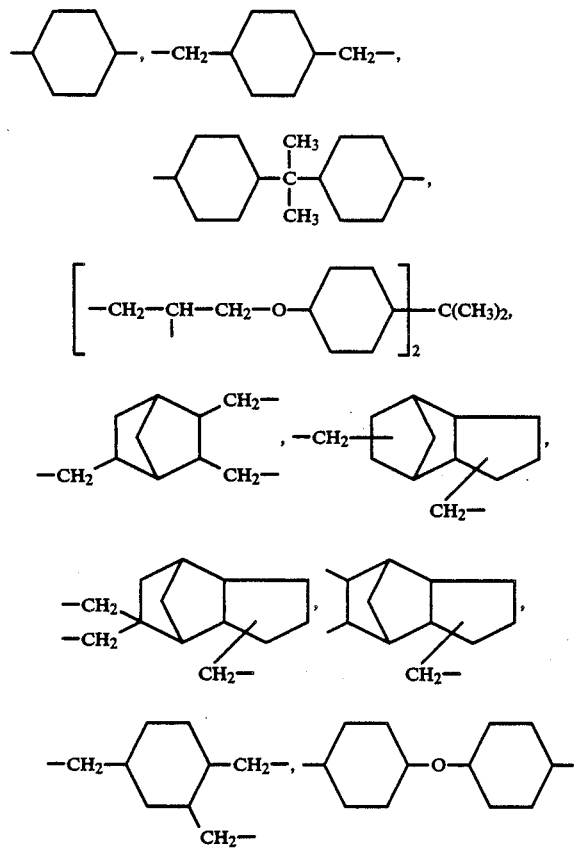

The radicals A can contain 1 or 2, preferably 1, oxygen atoms, preferably in the aliphatic or cycloaliphatic part, so that, for example, they represent aliphatic or cycloaliphatic ethers.

The following radicals A may be mentioned as particularly preferred: ethylene, propylene, 2,2-bismethylene-butan-1-yl, 2,2-bismethylene-propan-1-yl, 2,2-bismethylene-propane-1,3-diyl, 1,1'-oxy-bis-[(2,2-methylene)-propane-1,3-diyl], propane-1,2,3-triyl, 1,6-hexamethylene, 1,4-tetramethylene, 1,4-phenylene, xylylene, 1,4-cyclohexylene, 1,4-bismethylene-1,4-cyclohexane, 2,2-bis-(1,4-phenylene)propane, 3(4),8(9)-bismethylene-tricyclo[5.2.1.0$^{2.6}$]decane and isomers thereof, and 4 or 5,9-bismethylene-3,8-dimethyltricyclo[5.2.1.0$^{2.6}$]decane.

The radicals 2,2-bismethylene-butan-1-yl, propane-1,2,3-triyl, 2,2-bismethylenepropane-1,3-diyl and 3(4),8(9)-bismethylene-tricyclo[5.2.1.0$^{2.6}$]decane are particularly preferred.

In the group $R^4$ or $R^5$, lower alkyl can denote a straight-chain or branched hydrocarbon radical having 1 to about 6 carbon atoms. The following lower alkyl radicals may be mentioned as examples: methyl, ethyl, propyl, isopropyl, butyl, tert.-butyl, isobutyl, pentyl, isopentyl, hexyl and isohexyl. The methyl radical and the ethyl radical are preferred.

Lower alkoxy can denote a straight-chain or branched hydrocarbon radical which is bonded via oxygen and has 1 to about 6 carbon atoms. The following lower alkoxy radicals may be mentioned as examples: methoxy, ethoxy, propoxy, isopropoxy, butoxy, isobutoxy, pentoxy, isopentoxy, hexoxy and isohexoxy. The methoxy radical and ethoxy radical are preferred.

Halogen can denote fluorine, chlorine, bromine or iodine. Fluorine and chlorine are the preferred halogens.

The following are mentioned as examples of groups X:

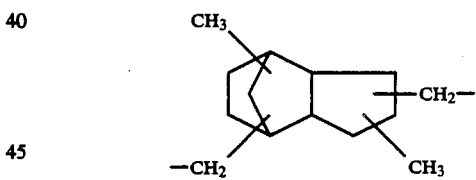

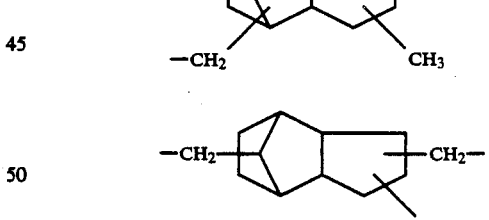

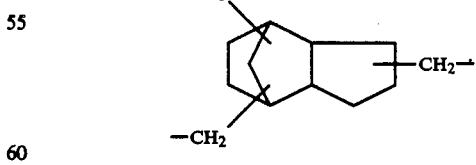

The radical

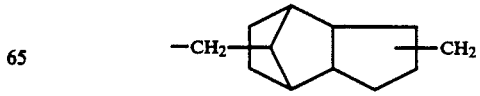

is the preferred group X.

A divalent hydrocarbon radical (Z) can denote a straight-chain or branched aliphatic hydrocarbon having 3 to 15 carbon atoms, preferably 3 to 10 carbon atoms. Optionally, the radical Z can contain 1 to 3 oxygen bridges, preferably 1 to 2 oxygen bridges. It is also possible for the radical Z to be substituted by 1 to 4, preferably 1 to 2, (meth)acrylate radicals. The following radicals may be mentioned as examples:

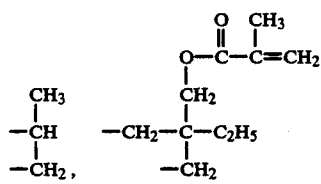

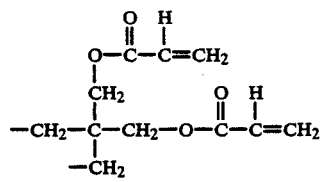

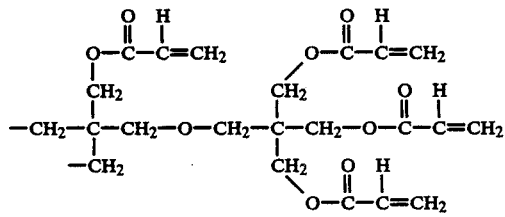

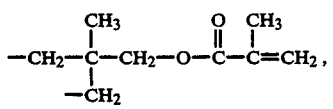

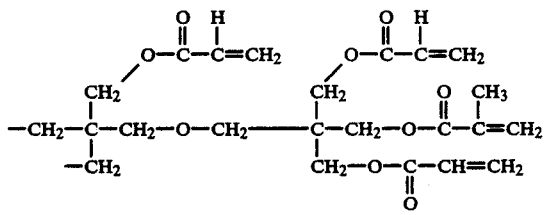

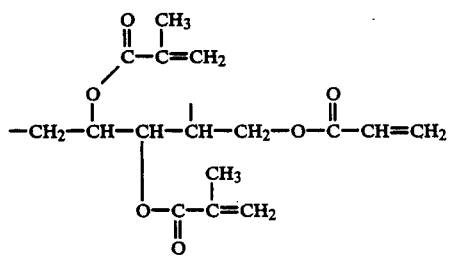

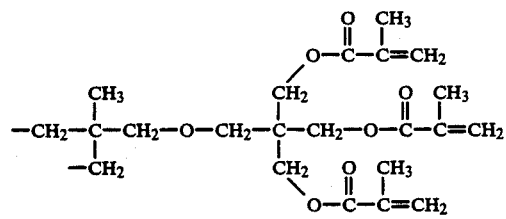

Those (meth)acrylic acid derivatives, containing urethane groups, of the formula (I) are preferred in which A is a straight-chain or branched aliphatic radical having 3 to 12 carbon atoms and optionally containing 1 to 3 oxygen bridges, an aromatic radical having 6 to 14 carbon atoms, an araliphatic radical having 7 to 26 carbon atoms or a cycloaliphatic radical having 6 to 14 carbon atoms, r represents the number of chains starting from A and denotes a number from 2 to 6, $R^1$ and $R^2$ are identical and denote hydrogen or are different and denote hydrogen and methyl, n denotes a number from 0 to 5, independently for each chain starting from A, X denotes the group

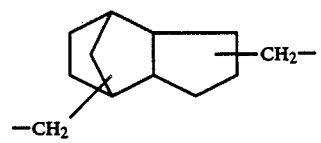

Z denotes a divalent straight-chain or branched aliphatic hydrocarbon radical which has 3 to 10 carbon atoms, can optionally contain 1 or 2 oxygen bridges and can optionally be substituted by 1 or 2 (meth)acrylate radicals, and $R^3$ denotes hydrogen or methyl, independently for each chain starting from A.

Those (meth)acrylic acid derivatives, containing urethane groups, of the formula (I) are particularly preferred in which A represents the 2,2-bismethylene-butan-1-yl radical, propane-1,2,3-triyl radical, 2,2-bis-methylenepropane-1,3-diyl radical or 3(4), 8(9)-bismethylene-tricyclo[5.2.1.0$^{2.6}$]decane radical, r represents the number of chains starting from A and denotes the number 3 or 4, $R^1$ and $R^2$ are identical and denote hydrogen or are different and denote hydrogen and methyl, n denotes a number from 0 to 5, independently for each chain starting from A, X denotes the group

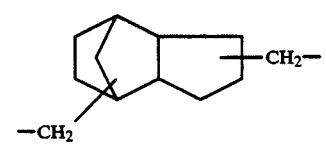

Z denotes a divalent straight-chain or branched aliphatic hydrocarbon radical which has 3 to 10 carbon atoms, can optionally contain 1 oxygen bridge and can optionally be substituted by 1 (meth)acrylate radical, and $R^3$ denotes hydrogen or methyl, independently for each chain starting from A.

The following (meth)acrylic acid derivatives, containing urethane groups, of tricyclo[5.2.1.0$^{2.6}$ decanes may be mentioned as examples:

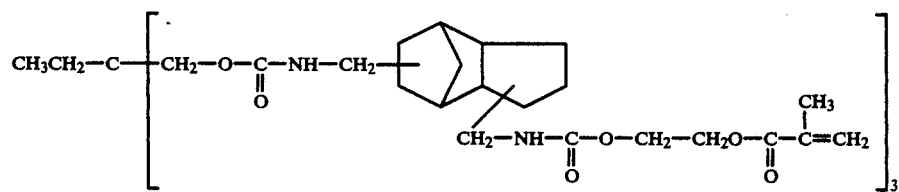
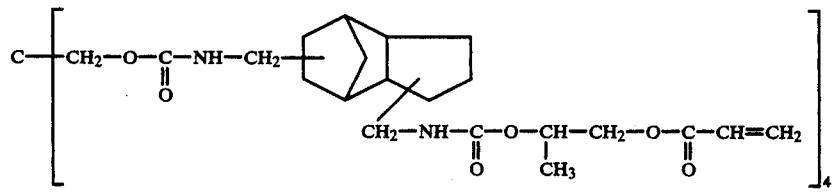
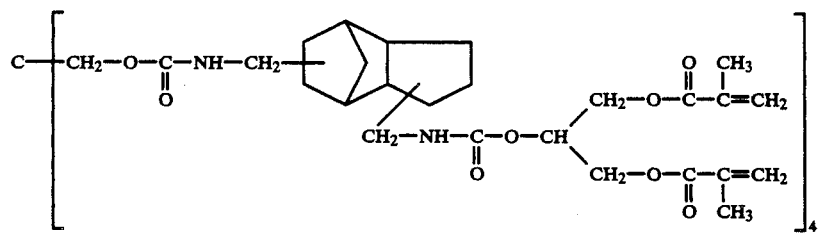
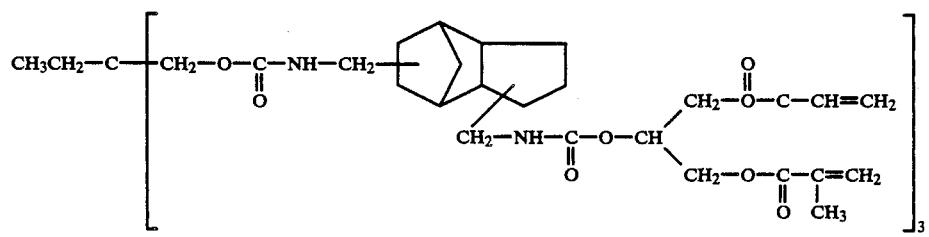
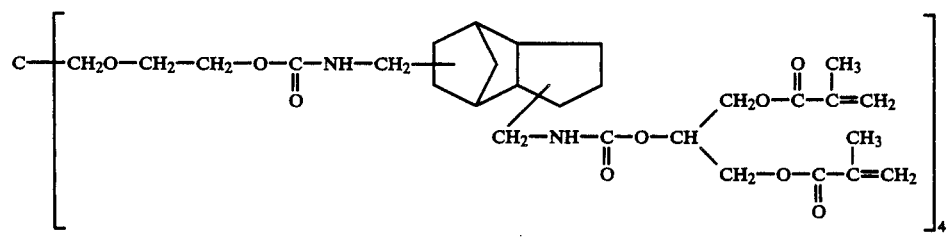
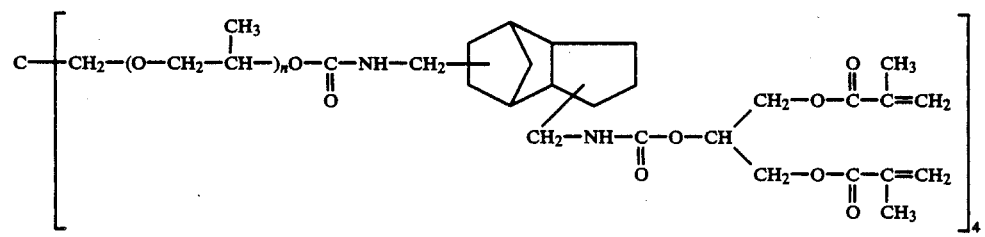
n = 1.225 (statistical mean for 4 chains)
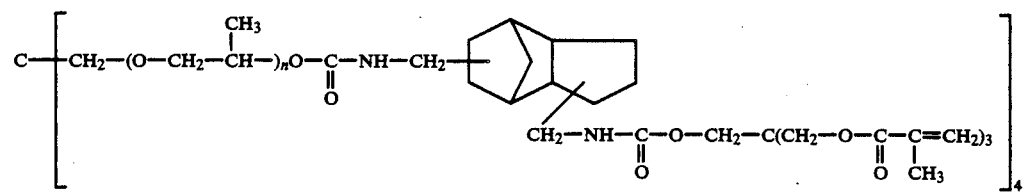
n = 1.225 (mean)

-continued
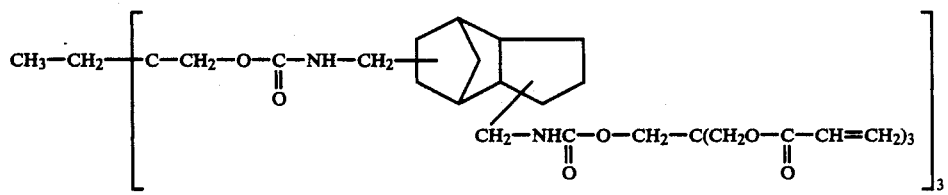
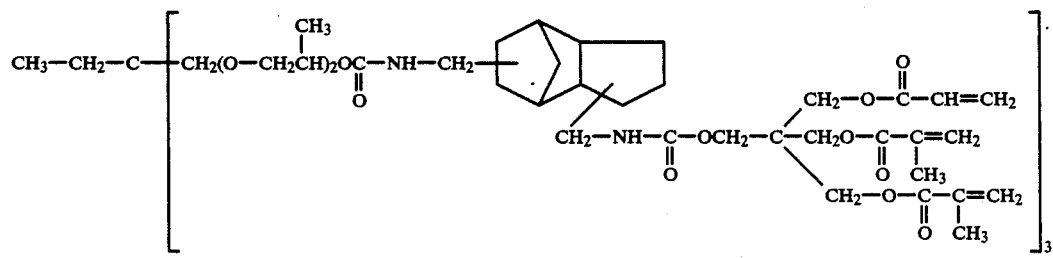
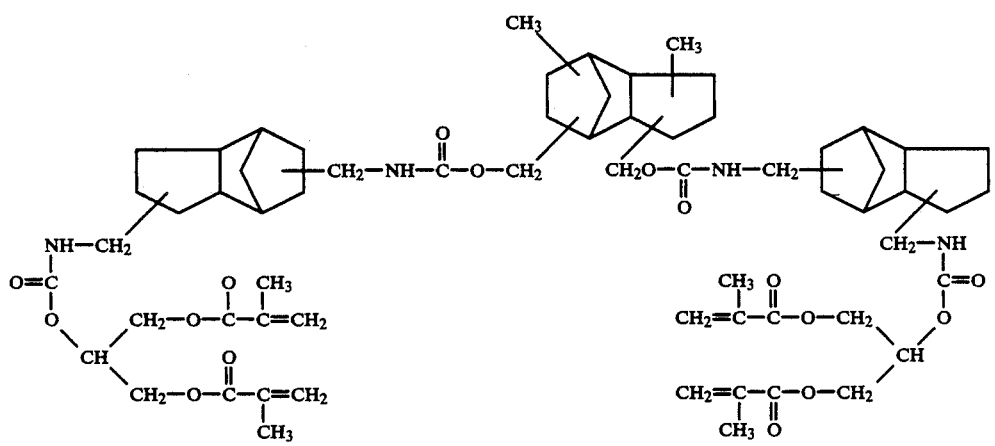
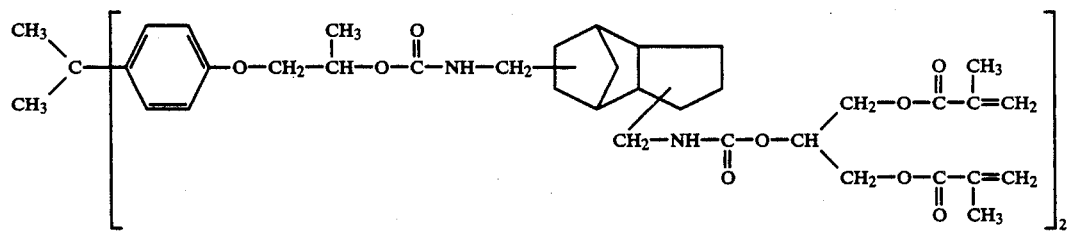
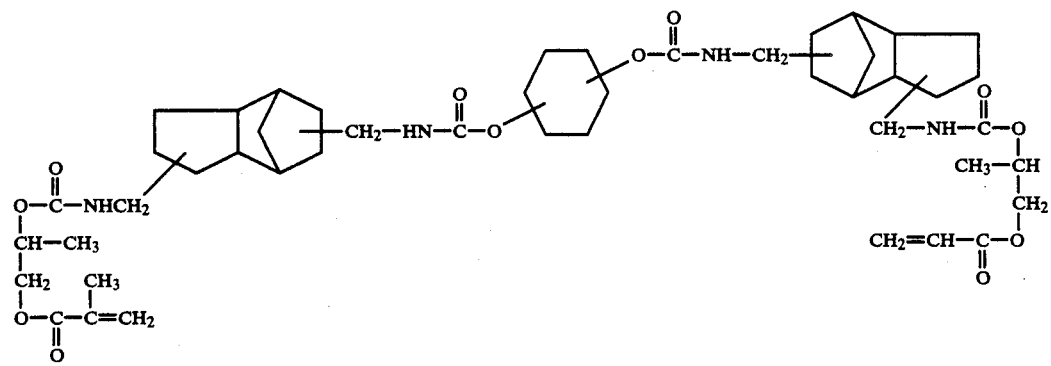

-continued

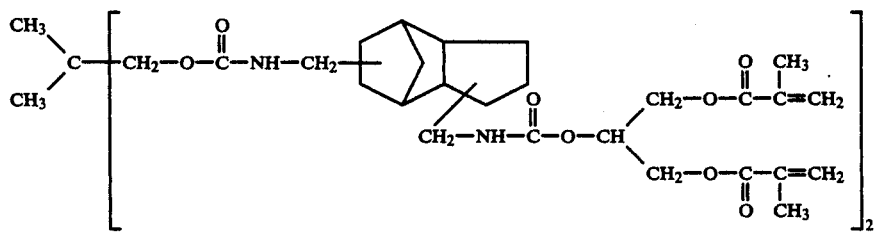

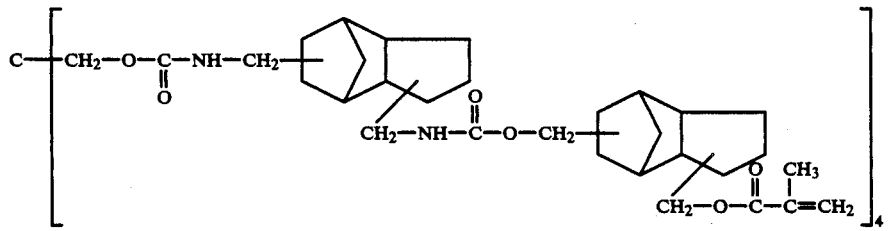

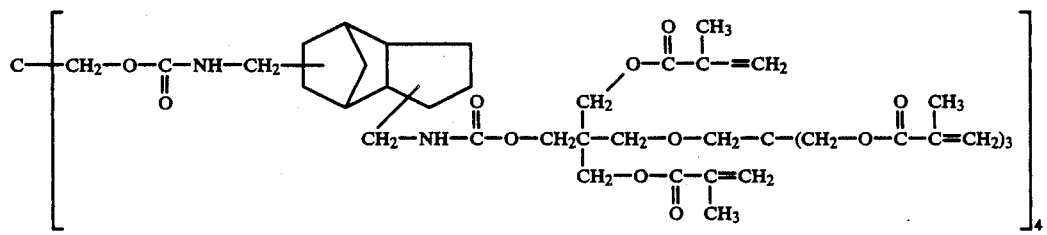

A process for the preparation of the (meth)acylic acid derivatives according to the invention, containing urethane groups, of tricyclo[5.2.1.0$^{2.6}$]decanes of the formula (I)

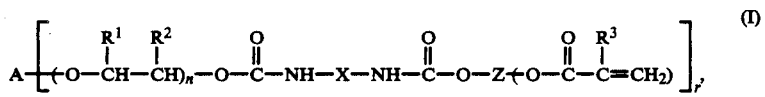

wherein

A is a straight-chain or branched aliphatic radical having 2 to 20 carbon atoms and optionally containing 1 to 3 oxygen bridges, an aromatic radical having 6 to 24 carbon atoms, an araliphatic radical having 7 to 26 carbon atoms or a cycloaliphatic radical having 6 to 26 carbon atoms, or represents the number of chains starting from A and denotes a number from 2 to 6, $R^1$ and $R^2$ are identical and denote hydrogen or are different and denote hydrogen and methyl, n denotes a number from 0 to 5, independently for each chain starting from A, X represents the group

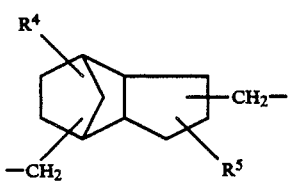

wherein $R^4$ and $R^5$ are identical or different and denote hydrogen, halogen, lower alkoxy, lower alkyl or trifluoromethyl, Z denotes a divalent straight-chain or branched aliphatic hydrocarbon radical which has 3 to 15 carbon atoms, can optionally contain 1 to 3 oxygen bridges and can optionally be substituted by 1 to 4 (meth)acrylate radicals, and $R^3$ denotes hydrogen or methyl, independently for each chain starting from A, has also been found, which is characterized in that a hydroxyalkyl (meth)acrylic acid ester of the formula (II)

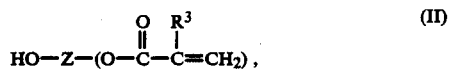

wherein

Z and $R^3$ have the meaning given above, is reacted with a diisocyanate of the formula (III)

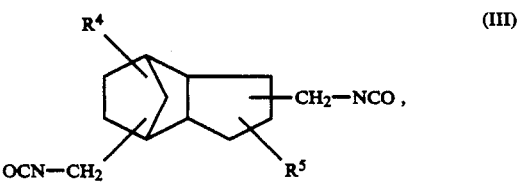

wherein $R^4$ and $R^5$ have the meaning given above, in a molar ratio of about 1:1 to 1:6 in an inert solvent in the presence of a catalyst and the isocyanatourethane thus formed is then reacted, after removal of unconverted diisocyanate, with a polyol of the formula (IV)

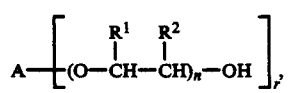

wherein

A, $R^1$, $R^2$, n and r have the meaning given above, in a molar ratio of OH groups to NCO groups of about 1:1.

(Meth)acrylic acid esters of the formula II are known per se and can be obtained, for example, by partial esterification of the corresponding polyols.

Diisocyanates of tricyclodecanes of the formula III are known per se and can be prepared, for example, by reacting the diamines of the tricyclodecanes with phosgene.

It is advantageous to purify the isocyanatourethane formed, if the diisocyanate III was employed in an excess, relative to the hydroxyalkyl (meth)acrylic acid ester II. The purification of the adduct of II and III is preferably carried out by extraction with aliphatic solvents having a boiling point below 120° C. under normal pressure, for example with pentane, n-hexane or isopentane.

Polyols of the formula IV are known per se (DE-A No. 2,931,925) or commercially available and can be prepared, for example, by oxyalkylation of the known polyols of the formula $A(OH)_r$, for example 2,2-bishydroxymethylbutane, 2,2-bishydroxymethyl-propane-1,3-diol, 3(4),8(9)-bishydroxymethyl-tricyclo[5.2.1.0$^{2.6}$]-decane and the like. In accordance with the method of preparation, the polyols IV can also be present as a product of variable degree of oxyalkylation.

Inert solvents are in general used for the process according to the invention. Acetone, chloroform, tetrahydrofuran, dioxane, methylene chloride, toluene and acetonitrile may be mentioned as examples. Chloroform, toluene, acetonitrile and acetone are particularly preferred.

In general, the process according to the invention is carried out with exclusion of water. A maximum quantity of water of less than 0.1% by weight, relative to the total quantity of the reactants, is particularly preferred.

The catalysts for the process according to the invention are in general metal salts of higher fatty acids. Preferred catalysts can, for example, be dibutyl-tin dilaurate, dibutyl-tin methoxide and tin (II) octoate. However, compounds with tertiary amino groups, such as triethylamine, pyridine, 2-methylpyridine, N,N-dimethylpiperazine and N,N-dimethyl-benzylamine can also be used as catalysts. Moreover, it is possible to employ titanium compounds such as tetrabutyl titanate.

In general, the catalyst is employed in a quantity of 0.1 to 2.5% by weight, preferably 0.1 to 1.5% by weight, relative to the total quantity of the reactants.

In a preferred embodiment, the process according to the invention can be carried out in the presence of a polymerization inhibitor. Polymerization inhibitors are known per se (Ullmanns Enzyklopädie der techn. Chemie [Ullmann's Encyclopedia of Industrial Chemistry], 4th edition, Verlag Chemie Weinheim, Volume 8, pages 19–45). 2,6-Di-tert.-butyl-4-methylphenol, hydroquinone and hydroquinone monomethyl ether may be mentioned as examples.

It is also possible to use oxygen, for example atmospheric oxygen, which is passed into the reaction mixture, as the polymerization inhibitor.

In general, the polymerization inhibitor is employed in a quantity of 0.01 to 1.0% by weight, preferably of 0.1 to 0.2% by weight.

The first stage of the process according to the invention is in general carried out in the temperature range from 0° to 120° C., preferably from 30° to 70° C. The second stage of the process according to the invention is in general carried out in the temperature range from 0° to 120° C., preferably from 30° to 70° C.

The process according to the invention is in general carried out under normal pressure. It is also possible, however, to carry out the process according to the invention under a reduced or superatmospheric pressure (for example in the pressure range from 0.1 to 10 bar).

The process according to the invention can be carried out, for example, as follows:

The (meth)acrylic acid ester of the formula (II) and, if appropriate, the polymerization inhibitor are dissolved in the inert solvent and added dropwise to the diisocyanate (III), which may be in solution. The catalyst is here added to one of the two reactants. The reactants are caused to react in a molar ratio of 1:1 to 1:6 and taken to complete conversion of the OH groups or the corresponding conversion of the isocyanate groups. The conversion of the isocyanate groups can be monitored in a known manner by IR spectroscopy and/or by titration.

An excess of diisocyanate can subsequently be extracted with n-hexane, n-pentane or other aliphatic solvents having a boiling point below 120° C. (under normal pressure).

In the second stage of the process according to the invention, the isocyanatourethane obtained in the first stage is, if appropriate after extraction of any excess diisocyanate present, reacted with a polyol of the formula (IV) in such a way that the number of hydroxyl equivalents of the polyol approximately corresponds to the number of the NCO equivalents, still present.

Preferably, $$\frac{0.9}{r} \text{ to } \frac{1.1}{r}$$

moles of the polyol IV are employed, relative to 1 mole of hydroxyalkyl (meth)acrylate II, r here having the above meaning of a number from 2 to 6.

The reaction is in general taken to complete conversion, so that neither free isocyanate nor polyol remain in the reaction mixture. When the conversion is complete, the reaction product is isolated by removal of the solvent. A preceding filtration or purification by means of adsorbents, for example active charcoal, bleaching earth, silica gel or aluminum oxide, is possible.

By the process according to the invention, a mixture of (meth)acrylic acid derivatives containing urethane groups is as a rule obtained, and these derivatives can be separated on adsorbents.

It is also possible to invert the order of the first and second stages of the above process. In this case, the diisocyanate III and the polyol IV are reacted in the first stage in a molar ratio of NCO:OH=2 to 10, preferably in a molar ratio of NCO:OH=2.0 to 4, until all the hydroxyl groups have been converted urethane groups.

Any excess of diisocyanate (if this was employed in an excess) which may be present is then extracted with the solvents mentioned, in the manner described above. The remaining NCO groups are then reacted in the second stage with a hydroxyalkyl (meth)acrylate II to give the (meth)acrylic acid ester according to the invention, the NCO and OH groups being stoichiometrically equivalent.

For the use, according to the invention, of the new urethane-(meth)acrylates in the dental field a separation of the reaction mixtures obtained is not required. The mixtures themselves can be used in an advantageous manner as a component of dental materials, for example tooth-filling materials.

The urethane-(meth)acrylates of tricyclo[5.2.1.0$^{2,6}$]-decanes, according to the invention, can be used as monomers for dental materials. Filling materials for teeth, tooth coatings and components for tooth replacements, preferably plastic teeth, may be mentioned as examples of dental materials. Depending on the field of application, the dental materials can contain further additives.

For the use as monomers for polymerizable tooth-filling compositions or coatings in the dental field, the (meth)acrylic acid derivatives according to the invention can be mixed with monomers known per se, for example in order to match the viscosity to the intended use. In this case, viscosities in the range from 60 to 10,000 mPas are preferred. This can be accomplished by mixing the monomers according to the invention with, if appropriate, a comonomer of low viscosity as a reactive diluent or solvent. In the mixture with comonomers, the compounds according to the invention are employed in a proportion of about 30 to about 90% by weight, preferably of 40 to 80% by weight. It is also preferred to employ mixtures of different (meth)acrylic acid esters according to the invention.

In order to obtain the desired viscosity, it is also possible to employ monomer mixtures which contain several comonomers.

The following comonomers may be mentioned as examples: glycerol di(meth)acrylate, triethylene glycol di(meth)acrylate, tetraethylene glycol di(meth)acrylate, 1,12-dodecanediol di(meth)acrylate, 1,6-hexanediol di(-meth)acrylate, diethylene glycol dimethacrylate, 2,2-bis-[p-(2'-hydroxy-3'-methacryloyloxypropoxy)-phenyl]-propane, 2,2-bis-[p-(2'-methacryloyloxyethoxy)-phenyl]-propane, trimethylolpropane tri(meth)acrylate, bis-(meth)acryloyloxyethoxymethyl-tricyclo[5.2.1.0$^{2,6}$]decane (DE-A No. 2,931,925 and DE-A No. 2,931,926).

Those comonomers are particularly preferred which have a boiling point above 100° C. under 13 mbar.

The polyfunctional (meth)acrylic acid esters according to the invention can, if appropriate as a mixture with the comonomers mentioned, be cured by methods known per se to give crosslinked polymers (Am. Chem. Soc., Symp. Ser. 212, 359–371 (1983)). For the so-called redox polymerization, a system comprising a peroxidic compound and a reducing agent, for example based on tertiary aromatic amines, is suitable. Examples of peroxides are: dibenzoyl peroxide, dilauroyl peroxide and di-4-chlorobenzoyl peroxide.

Examples of tertiary aromatic amines which may be mentioned are N,N-dimethyl-p-toluidine, bis-(2-hydroxyethyl)-p-toluidine, bis-(2-hydroxyethyl)-3,5-dimethylaniline and N-methyl-N-(2-methylcarbamoyloxypropyl)-3,5-dimethylaniline. The concentrations of the peroxide or the amine are advantageously selected such that they amount to 0.1 to 5% by weight, preferably 0.5 to 3% by weight, relative to the monomer mixture. The monomer mixtures containing peroxide or amine are stored separately until they are used.

The monomers according to the invention can also be caused to polymerize by exposure with light or visible light (for example in the wavelength range from 230 to 650 nm). Examples of suitable initiators for the photoinitiated polymerization are benzil, benzil dimethylketal, benzoin monoalkyl ethers, benzophenone, p-methoxybenzophenone, fluorenone, thioxanthone, phenanthrenequinone and 2,3-bornanedione (camphorquinone), optionally in the presence of activators having a synergistic effect, such as N,N-dimethylaminoethyl methacrylate, triethanolamine, 4-N,N-dimethylaminobenzenesulphonic acid diallylamide. The photopolymerization procedure is described, for example, in DE-A No. 3,135,115.

Apart from the initiators described above, light stabilizers and other stabilizers, known per se for this application, can be added to the (meth)acrylic acid derivatives according to the invention.

Light stabilizers are described by way of example in (Gachter, Muller, Taschenbuch der Kunststoff-Additive, [Handbook of Plastics Additives], 2nd edition, Carl Hanser Verlag). The following light stabilizers may be mentioned as examples: Cyasorb UV9$^R$, Tinuvin P$^R$, Tinuvin 770$^R$, Tinuvin 622$^R$ and Tinuvin 765$^R$.

Other stabilizers are described by way of example in (Ullmanns Encyclopädie der technischen Chemie [Ullmann's Encyclopedia of Industrial Chemistry], 4th edition, Volume 8). The following stabilizers may be mentioned as examples: 2,6-di-tert.-butylphenol, 2,6-di-tert.-butyl-4-methylphenol, 2,6-di-octadecyl-4-methylphenol, 1,1'-methylene-bis-(naphth-2-ol) and others.

The light stabilizers and other stabilizers can each be employed in a quantity of 0.01 to 0.5 parts by weight, relative to 100 parts by weight of monomer mixture.

The monomer mixtures can be employed as coating agents (dental varnishes) without added fillers.

For the use as tooth-filling compositions, fillers are in general added to the monomer mixtures obtained. In order to be able to obtain a high degree of filling, monomer mixtures having a viscosity in the range from 60 to 10,000 mPas are particularly advantageous.

Preferably, inorganic fillers are added to the (meth)acrylic acid derivatives according to the invention. Examples which may be mentioned are rock crystal, cristobalite, fused quartz, highly disperse silica, aluminum oxide and glass ceramics, for example glass ceramics containing lanthanum and zirconium (DE-A No. 2,347,591). The inorganic fillers are preferably pretreated with an adhesion promoter in order to improve the bonding with the polymer matrix of the polymethacrylate. Adhesion promotion can be accomplished, for example, by a treatment with organosilicon compounds (Progress in Organic Coatings 11, 297–308 (1983)). Preferably, 3-methacryloyloxypropyl-trimethoxysilane is used. The fillers for the tooth-filling compositions according to the invention have in general a mean particle diameter of 0.01 to 100 μm, preferably of 0.03 to 50 μm and particularly preferably of 0.03 to 5 μm. It can also be advantageous to employ several fillers of different particle diameters and/or different silane contents side by side.

The proportion of filler in the tooth-filling composition is in general 5 to 85% by weight, preferably 50 to 80% by weight.

To prepare the tooth-filling compositions, the components are mixed, using commercially available kneading machines.

The proportion of the urethane-(meth)acrylates according to the invention in the tooth-filling compositions is in general 5 to 70% by weight, relative to the filling composition.

The urethane-(meth)acrylic acid derivatives, according to the invention, of tricyclo[5.2.1.0$^{2.6}$]decanes can also be used as components in the preparation of tooth replacements.

In this case, the monomers according to the invention are combined with the normally used constituents known per se. Preferably, the monomers are employed as a mixture with alkyl methacrylates, such as methyl methacrylate. In addition, bead polymers known per se can also be added. To match the tooth color, known inorganic and organic color pigments and opacitying agents can be added. The use of light stabilizers and other stabilizers is also possible.

The plastic teeth are prepared by free-radical polymerization of the dental compositions with shaping.

Processing is possible both by means of injection methods and swaging methods and is in general carried out by the usual preparation methods for teeth, based on poly(methyl methacrylate), for example by thermal polymerization using polymerization initiators known per se, for example those based on peroxides and azo compounds, such as dibenzoyl peroxide, dilauroyl peroxide, cyclohexyl percarbonate and azo-bis-isobutyronitrile. Mixtures of polymerization initiators having different decomposition temperatures are also highly suitable.

The dental materials prepared from the (meth)acrylic acid esters according to the invention are distinguished by a high resistance to mechanical stress and a high abrasion resistance.

PREPARATION EXAMPLES

Example 1

Reaction of the (1:1) adduct of glycerol dimethacrylate and bis-(isocyanatomethyl)-tricyclo[5.2.1.0$^{2.6}$]decane with pentaerythritol.

22.8 g of commercially available glycerol dimethacrylate, 0.1 g of dibutyl-tin dilaurate and 20 mg of 2,6-di-tert.-butyl-4-methylphenol (ionol) are dissolved in 30 ml of dried methylene chloride and added dropwise at 40° to 45° C. to 24.6 g of bis-isocyanatomethyl-tricyclo[5.2.1.0$^{2.6}$]decane. The mixture is stirred at this temperature until half the NCO groups have reacted. The NCO groups are determined in the known manner by reaction with dibutylamine and back-titration of the excess dibutylamine with hydrochloric acid. At the desired conversion, a further 30 ml of methylene chloride and 3.4 g of pentaerythritol are added. The mixture is stirred at 40° to 45° C. (for about 48 hours) until isocyanate is no longer detectable in the IR spectrum. The reaction product is filtered over activated charcoal or silica gel and freed of solvent. A white solid is obtained.

Melting point 70° to 75° C.

80 MHZ $^1$H-NMR spectrum (CDCl$_3$) [ppm]:

0.8–2.5 Protons of the tricyclodecane system, 56 H

| | | |
|---|---|---|
| 1.94 | CH$_3$—C(=CH$_2$)— | 24 H |
| 3.0 | —CH$_2$—NH—C(=O)—O— | 16 H |
| 4.0–4.4 | —CH$_2$—O—C(=O)—NH and O—CH$_2$—CH—CH$_2$—O | 24 H |
| 4.8–5.0 | NH, | 8 H |
| 5.1–5.4 | O—CH$_2$—CH—CH$_2$—O | 4 H |
| 5.5–5.65 and 6.05–6.25 | CH$_2$=C(CH$_3$)— | 16 H |

Example 2

Reaction of the (1:1) adduct of glycerol dimethacrylate and bis-isocyanatomethyl-tricyclo[5.2.1.0$^{2.6}$]decane with trimethylolpropane.

22.8 g of glycerol dimethacrylate, 20 mg of ionol and 0.1 g of dibutyl-tin dilaurate are dissolved in 30 ml of dried chloroform and added dropwise at 40° to 50° C. to 24.6 g of bis-isocyanatomethyl-tricyclo[5.2.1.0$^{2.6}$]decane. The mixture is stirred at 40° to 50° C. until half the NCO groups have reacted (about 3 hours). 4.46 g of trimethylolpropane in 30 ml of chloroform are then added.

A reaction temperature of 40° to 50° C. is maintained up to complete conversion of the NCO groups (monitoring by IR spectroscopy). After the reaction has ended, the mixture is filtered over silica gel if necessary and the solvent is stripped off in a rotary evaporator. The product is a colorless solid.

$^1$H-NMR Spectrum in CDCl$_3$/TMS [ppm]:

0.7–2.6 Protons of the tricyclodecane skeleton

| | | |
|---|---|---|
| 0.7–2.6 | Protons of the tricyclodecane skeleton and CH$_2$—CH$_3$—C— | 47 H |
| 1.94 | CH$_3$—C(=CH$_2$)— | 18 H |
| 3.0 | —CH$_2$—NH—C(=O)—O— | 12 H |
| 3.9–4.1 and 4.2–4.45 | —CH$_2$—O—C(=O)— | 18 H |
| 4.8–5.1 | NH, | 6 H |
| 5.15–5.45 | O—CH(CH$_2$O—)(CH$_2$O—) | 3 H |

| 5.5-5.65 and 6.05-6.2 | 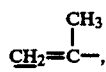 $\underline{CH_2}$=C— $\vert$ $CH_3$ | 12 H |
|---|---|---|

Example 3

Reaction of the (1:1) adduct of glycerol dimethacrylate and bis-isocyanatomethyl-tricyclo[5.2.1.0$^{2.6}$]decane with bis-hydroxymethyl-tricyclo[5.2.1.0$^{2.6}$]decane (TCD-DM).

22.8 g of glycerol dimethacrylate, 23 mg ionol and 0.1 g of dibutyl-tin dilaurate are dissolved in 30 ml of dried methylene chloride and added dropwise at 40° to 45° C. to 24.6 g of bis-isocyanatomethyl-tricyclo[5.2.1.0$^{2.6}$]-decane. After half the isocyanate groups have been converted, 9.8 g of TCD-DM in 30 ml of methylene chloride are added. After about 24 hours at 40° to 45° C., all the NCO groups have been converted. The solvent is stripped off in a rotary evaporator. The product is isolated as a colorless solid.

Melting point: 65° to 70° C.

Molecular weight (by osmometry: 1,104 (calculated 1,144).

Example 4

Reaction of the (1:1) adduct of 2-hydroxyethyl methacrylate (HEMA) and bis-isocyanatomethyl-tricyclo[5.2.1.0$^{2.6}$]decane with trimethylolpropane.

26 g of dehydrated HEMA are dissolved in 53 g of chloroform and, after 34 mg of ionol have been added, added dropwise at 45° C. to 49.2 g of bis-isocyanatomethyl-tricyclo[ 5.2.1.0$^{2.6}$]decane. After about 24 hours, of the NCO groups have been converted. 8.9 g of trimethylolpropane and 0.1 g of tin octoate are then added, and the mixture is stirred for a further 24 hours at 45° C. The reaction mixture is filtered over silica gel and, after the addition of 80 g of triethylene glycol dimethacrylate (TEGDMA), freed of solvent up to constant weight. The product has a viscosity of about 1,000 mPa.s at 25° C.

Example 5

Reaction of the (1:1) adduct of glycerol dimethacrylate and bis-isocyanatomethyl-tricyclo[5.2.1.0$^{2.6}$]decane with propoxylated pentaerythritol.

34.2 g of glycerol dimethacrylate, 34 mg of ionol and 0.1 g of tin octoate are dissolved in 51 g of chloroform and added dropwise at 50° C. to 36.9 g of bis-isocyanatomethyl-tricyclo[5.2.1.0$^{2.6}$]decane. After half the NCO groups have been converted, 15.8 g of the adduct of 1 mole of pentaerythitol and 4.9 moles of propylene oxide (OH number=534 mg of KOH/g) are added. After about 18 hours at 50° C., the isocyanate has been fully converted. 50 g of TEGDMA are added and the solvent is removed in vacuo up to constant weight.

Example 6

44.7 g of pentaerythritol triacrylate and 35 mg of ionol are dissolved in 91 g of chloroform and added dropwise at 50° C. to 36.9 g of bis-isocyanatomethyl-tricyclo[5.2.1.0$^{2.6}$]decane and 50 mg of tin(II) octoate. When half the NCO groups have been converted, 6.7 g of trimethylolpropane in 50 ml of chloroform are added and the mixture is stirred at 50° C. until the NCO groups have been fully converted. Activated charcoal is then stirred in. After addition of 97.6 g of TEGDMA, the filtrate is concentrated in vacuo up to constant weight.

APPLICATION EXAMPLES

Example 7

Preparation of sealer solutions (a) Light-curing dental varnish (sealer)

0.5% of N,N-diallyl-p-dimethylaminobenzenesulphonic acid amide, 0.2% of camphor-quinone and 0.125% of benzil dimethylketal are dissolved in a mixture of 45 parts by weight of triethylene glycol dimethacrylate and 55 parts by weight of the monomer from Example (1).

On irradiation with a commercially available dental lamp (Translux, from Messrs. Kulzer), the liquid cures to give a solid plastic. According to DIN 13 922, this cured sealer solution has a flexural strength of 95 N/mm$^2$ and a modulus of elasticity of 2,100 N/mm$^2$.

The sealer solution prepared correspondingly from 59.9 parts by weight of monomer from Example 3) and 40.1 parts by weight of triethylene glycol dimethacrylate has a flexural strength of 105 N/mm$^2$ and a modulus of elasticity of 2,460 N/mm$^2$.

(b) Redox-curing system

Catalyst solution

2% of benzoyl peroxide are dissolved in a mixture of 45 parts by weight of triethylene glycol dimethacrylate and 55 parts by weight of monomer from Example (1).

Activator solution 2.15% of N-methyl-N-β-(methylcarbamoyloxy)-propyl-3,5-dimethylaniline are dissolved in a mixture of 45 parts by weight of triethylene glycol dimethacrylate and 55 parts by weight of monomer from Example (1).

A mixture of equal parts of catalyst solution and activator solution cures within 1 minute.

Example 8

Composition for filling tooth cavities (a) Redox-curing system

Peroxide paste

2% of benzoyl peroxide are dissolved in a mixture of 55 parts by weight of monomer from Example (1) and 45 parts by weight of triethylene glycol dimethacrylate. 10 g of a silanized glass ceramic are processed with 4 g of this solution to give a paste.

Amine paste 1.3% of N-methyl-N-β-(methylcarbamoyloxy)-propyl-3,5-dimethylaniline are dissolved in a mixture of 55 parts by weight of monomer from Example (1) and 45 parts by weight of triethylene glycol dimethacrylate.

4 g of this solution are processed with 10 g of a silanized glass ceramic to give a paste. When equal parts of amine paste and peroxide paste are mixed with one another, the mixture cures within 2 minutes. The pastes can be colored with pigments and are suitable for filling tooth cavities.

(b) Light-curing system 0.5% of N,N-diallyl-p-dimethylaminobenzenesulphonic acid amide, 0.2% of camphor quinone and 0.125% of benzil dimethylketal are dissolved in a mixture of 55 parts by weight of monomer from Example 1 and 45 parts by weight of triethylene glycol dimethacrylate. 10 g of a silanized glass ceramic are processed with 4 g of this solution to give a paste. When this composition is irradiated with a commercially available dental lamp (Translux, from Messrs. Kulzer), a layer of 7 mm is fully cured after 40 seconds.

The light-curing paste is cured according to DIN 13 922 to give a dental plastic which shows a flexural strength of 135 N/mm$^2$ and a modulus of elasticity of 12,458 N/mm$^2$.

The paste prepared analogously from 60 parts by weight of monomer from Example 2 and 40 parts by weight of triethylene glycol dimethacrylate gives a flexural strength of 124 N/mm$^2$ and a modulus of elasticity of 11,107 N/mm$^2$.

Example 9

Wallace hardness test of cured sealer solutions

The urethane-(meth)acrylates of tricyclodecanes from the preparation examples are adjusted with triethylene glycol dimethacrylate to a viscosity appropriate for practice and are activated with 0.5% by weight of N,N-diallyl-p-dimethylaminobenzenesulphonic acid amide, 0.2% by weight of camphor quinone and 0.125% by weight of benzil dimethylketal. The activated mixtures were cured by means of a commercially available dental lamp (Translux, from Messrs. Kulzer) to give solid specimens, on which the hardness test by the Wallace method was carried out.

The Wallace method serves for determining the indentation hardness of plastics. A Vickers diamond is applied under an initial load of 1 p to the surface and then loaded for 60 seconds with a main load of usually 100 p. As a measure of the indentation resistance, the indentation depth of the diamond under the main load is measured in μm. In contrast to the measurements of the Vickers or Brinell hardness, where the test force is related to the dimensions of the permanent deformation, the elastic deformation and the permanent deformation of the plastic are covered by the Wallace method. This method is more suitable for the characterization of materials for applications in the dental field than hardness tests which cover only the permanent deformation. The smaller the penetration depth $H_W$, the harder is the material.

TABLE 1

| Monomer | Wallace hardnesses Monomer/TEGDMA* [Parts by weight] | Wallace hardness [μm] |
|---|---|---|
| Monomer from 1 | 55/45 | 13.0 |
| Monomer from 2 | 60/40 | 11.9 |
| Monomer from 3 | 59.9/40.1 | 15.5 |
| Monomer from 6 | 47.5/52.5 | 12.5 |
| Bis-GMA$^{(1)}$ | 62.0/38.0 | 23.0 |

*TEGDMA = Triethylene glycol dimethacrylate
$^{(1)}$2,2-bis-[4'-(3'-methacryloyloxy-2'-hydroxypropoxy)-phenyl]propane (comparison example)

Example 10

Preparation of plastic teeth 60 parts by weight of a monomer mixture, which was prepared from 45% by weight of triethylene glycol dimethacrylate and 55% by weight of the urethane-methacrylic acid derivative from Example 1, are mixed with 1 part by weight of dibenzoyl peroxide and 40 parts by weight of a highly disperse silica which has been silanized with 5% of 3-methacryloyloxypropyl-trimethoxysilane (BET surface area: 50 m$^2$/g).

The activated mixture is injected into a tooth mold and cured at 130° C. within 6 minutes. The plastic teeth obtained show a particularly high abrasion resistance.

What is claimed is:

1. A dental material containing a (meth) acrylic acid derivative, containing urethane groups, of the formula $$A \left[ (O-CH(R^1)-CH(R^2))_n -O-\overset{O}{\underset{\|}{C}}-NH-X-NH-\overset{O}{\underset{\|}{C}}-O-Z- \right.$$
$$\left. (O-\overset{O}{\underset{\|}{C}}-\overset{R^3}{\underset{|}{C^*}}CH_2) \right]_r$$

wherein

A is a straight-chain or branched aliphatic radical having 3 to 12 carbon atoms or is a straight chain or branched aliphatic radical having 3 to 12 carbon atoms containing 1 to 3 oxygen bridges, an aromatic radical having 6 to 14 carbon atoms, an araliphatic radical having 7 to 26 carbon atoms or a cycloaliphatic radical having 6 to 14 carbon atoms, r represents the number of chains starting from A and denotes a number from 2 to 6, $R^1$ and $R^2$ are identical and denote hydrogen or are different and denote hydrogen and methyl, n denotes a number of 0 to 5 for each chain starting from A, X denotes the group Z denotes a divalent straight-chain or branched aliphatic hydrocarbon which has 3 to 10 carbon atoms or denotes a divalent straight-chain or branched aliphatic hydrocarbon which has 3 to 10 carbon atoms and which contains 1 or 2 oxygen bridges, Z can be unsubstituted or substituted by 1 to 2 (meth) acrylate radicals, and $R^3$ denotes hydrogen or methyl for each chain starting from A.

2. A dental material according to claim 1, wherein

A represents the 2,2-bismethylene-butan-1-yl radical, propane-1,2,3-triyl radical, 2,2-bismethylenepropane-1,3-diyl radical or 3(4), 8, (9)-bismethylene-tricyclo[5.2.1.0$^{2.6}$]decane radical, r represents the number of chains starting from A and denotes the number 3 or 4, $R^1$ and $R^2$ are identical and denote hydrogen or are different and denote hydrogen and methyl, n denotes a number from 0 to 5, independently for each chain starting from A, X denotes the group

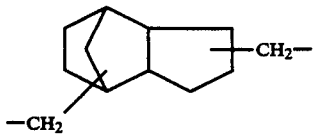

3. A dental material according to claim 1, further comprising a low viscosity comonomer which is a reactive diluent or solvent.

4. A dental material according to claim 3, wherein the low viscosity comonomer is a di(meth) acrylate or a tri(meth)acrylate.

5. A dental material according to claim 1, further comprising an alkyl methacrylate.

6. A dental material according to claim 1, further comprising a inorganic pigment, an organic color pigment or opacifying agent.

7. A dental material according to claim 1 further conprising fillers.

* * * * *